US00PP08748P

United States Patent [19]

Izhar et al.

[11] Patent Number: Plant 8,748

[45] Date of Patent: May 24, 1994

[54] STRAWBERRY PLANT VIRGINIA

[75] Inventors: Shamay Izhar; Eva Izsak, both of Rehovot, Israel

[73] Assignee: The Volcani Center, State of Israel, Ministry of Agriculture, Bet Dagan, Israel

[21] Appl. No.: 823,802

[22] Filed: Jan. 22, 1992

[30] Foreign Application Priority Data

Apr. 10, 1991 [IL] Israel ..... 1680/91

[51] Int. Cl.[5] ..... A01H 5/00

[52] U.S. Cl. ..... Plt./49

[58] Field of Search ..... Plt. 48, 49

[56] References Cited

PUBLICATIONS

Bailey, L. H., "Fragaria" *The Standard Cyclopedia of Horticulture* vol. II The Macmillan Co., N.Y. 1935 pp. 1271–1273.

Howard, C. M. and Albregts, E. E., 1980, "Dover" strawberry. HortScience 15(4):540.

Dubinsky, V., The Influence of daylength and night temperature on early flowering in strawberry. M.Sc. Thesis, The Hebrew University of Jerusalem; Rehovot, Isreal (Hebrew original and English translation).

Bringhurst, R. S. and Voth, V., 1989, California Strawberry Cultivars. Fruit Var. J. 43(1):12–19.

Izsak, E. and Izhar, S., Registration No. 370/82, registered Nov. 26, 1984 under State of Israel Plant Breeders' Rights Law of 1973 for strawberry variety 'Rachel'.

Izsak, E., 1978, "Nurit": new early variety for export, Hassadeh 59:433–446 (Hebrew original and English translation).

Izsak, E. and Izhar, S., 1983, The importance of day length and night temperature on earliness in strawberry. Hassadeh 63:2100–2103 (Hebrew original and English translation).

Izsak, E. and Izhar, S., 1984, Breeding and testing of early strawberry varieties in the central and the northern Negev regions. Hassadeh 64:1774–1777 (Hebrew original and English translation).

Izsak, E. and Izhar, S., 1984, "Rachel": a new early variety of strawberry for export. Hassadeh 64:1778–1781 (Hebrew original and English translation).

*Primary Examiner*—James R. Feyrer

[57] ABSTRACT

A new and distinct variety of strawberry (Fragaria L.) called "Virginia" is disclosed. The variety is a cross between "Chandler" and "230" which results in a variety that flowers several months earlier than most other known strawberry varieties.

2 Drawing Sheets

BACKGROUND OF THE INVENTION

The present invention relates to a new and distinct variety of strawberry (Fragaria L.) called "Virginia". The variety was developed from an organized scientifically designated breeding program carried out at the Agricultural Research Organization, the Volcani Center, Bet Dagan, Israel. The variety is the product of selection of seedings resulting from crosses between the strawberry varieties "Chandler" and "230". The variety was asexually vegetatively propagated through runners and the reproduction ran true.

SUMMARY OF THE INVENTION

The new variety "Virginia" is able to grow in September and produce fruit starting in November and lasting until summer. The production of fruit beginning in November is two months earlier than short-day strawberry varieties and within a similar time frame of strawberry varieties "Shalom" (U.S. Plant Pat. No. 7,876), "Smadar" (U.S. Plant Pat. No. 7,865), "Saaid" (U.S. Plant Pat. No. 7,870), "Dorit" (U.S. Plant Pat. No. 7,689), "Sharon" (U.S. Plant Pat. No. 7,881). The fruit of the "Virginia" variety is characterized by good taste, good shape and size as well as a long shelf life.

DETAILED BOTANICAL DESCRIPTION OF THE INVENTION

Figure 1:
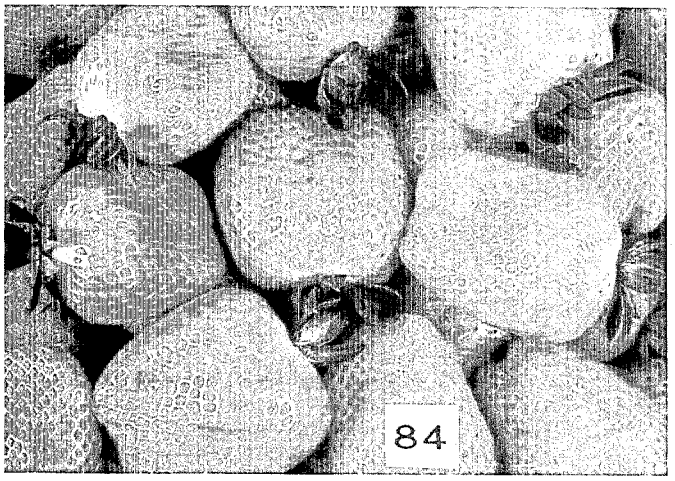
FIG. 1.—Photograph of the "Virginia" variety illustrating the fruit.
Figure 2:
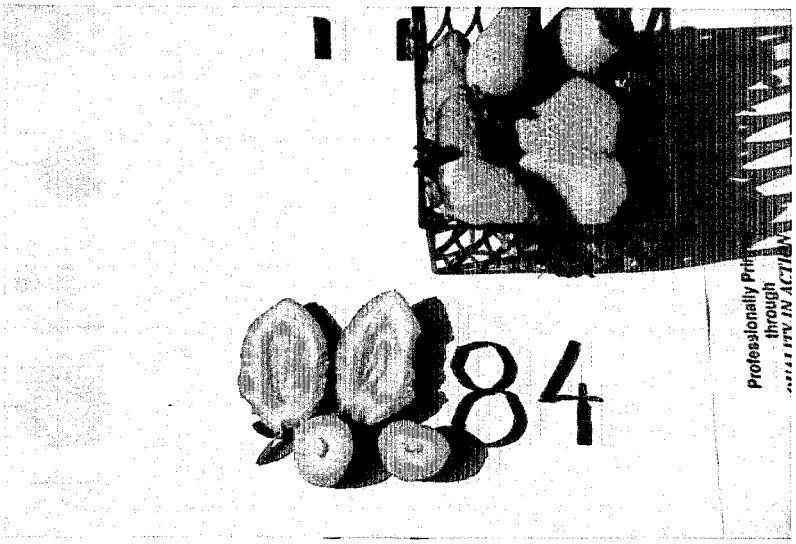
FIG. 2.—Photograph of the "Virginia" variety illustrating a cross-section of the fruit.
Figure 3:
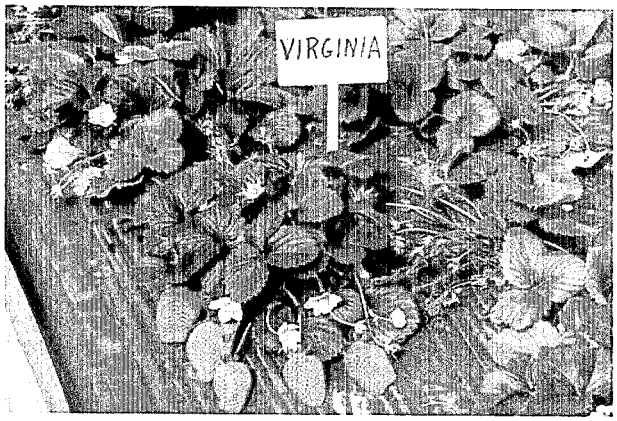
FIG. 3.—Photograph of the "Virginia" variety illustrating the entire plant with foliage, flowers and fruit.

The "Virginia" variety was grown in winter under polyethylene tunnels in Israel. "Virginia" is a an infra short-day strawberry variety. Infra short-day varieties are induced to initiate flower bud primordia in response to relatively long light regimes (but under short-day conditions) and are relatively insensitive to night temperatures. Flowering and fruit production is not affected by the use of polyethylene wind tunnels. This production procedure is utilized in normal agricultural practices by the skilled artisan and does not involve temperature or light control. Mother plants were stored at 0° C. from January through April. They were then planted in the nursery without further treatment. Runners with plantlets were produced during summer. These young plantlets were collected from the nursery in September and transferred to raised beds. Average temperatures at that time of the year are 30° C. during the day and 22° C. at night. Water and fertilizers were applied through drip irrigation. An August 25 and September 15 with the approximate date of flowering on October 1–10 and the approximate date of first fruiting on November 1. "Virginia" flowering is not induced by chilling, but by natural exposure to shortening day length. Color readings described herein were taken under natural light conditions and color identifications were made by reference to The Royal Horticultural Society Colour Chart (RHSCC) except where common terms of color definition are employed.

The pertinent characteristics of the present invention are presented in Table 1 and Table 2. Additionally, the variety "Virginia" (1) has no tendency toward fruit malformation; (2) disease resistance appears normal in that no particular problematic conditions arose during trials; and (3) the type of bearing is not remontant (e.g., "Virginia" blooms perpetuously, during late fall and winter).

The fruit is longer than broad, with first order and second order fruit possessing similar shapes (Table 2). The fruit is medium to firm with a red color (Table 2).

The variety "Virginia" flowers several months earlier than known strawberry varieties. One of the closest known varieties would be "Karina" (Table 1), and the new varieties mentioned supra; e.g., U.S. Plant Pat. No. 7,881 ("Sharon"), U.S. Plant Pat. No. 7,876 ("Shalom"), U.S. Plant Pat. No. 7,865 ("Smadar"), U.S. Plant Pat. No. 7,870 ("Saaid"), and U.S. Plant Pat. No. 7,869 ("Dorit"). Additionally, early flowering results in early fruit production for "Virginia" and the two varieties; "Ofra", subject of U.S. Plant Patent Application Ser. No. 07/823,638, filed Jan. 22, 1992, and "Nama", subject of U.S. Plant Patent Application Ser. No. 07/823,721, filed Jan. 22, 1992. Total Soluble Solids (TSS), marketable appearance, fruit color, sepal appearance, firmness, pressure defects and general health are presented in Table 3 by comparison to the co-pending varieties as well as the short-day variety, "Douglas" (U.S. Plant Pat. No. 4,487).

TABLE 1

PLANT CHARACTERISTICS OF "VIRGINIA"

| MORPHOLOGICAL TRAIT | DESCRIPTION[a] | COMPARABLE VARIETY[b] |
|---|---|---|
| Classification | Botanical-*Fragaria* L. | |
| Plant habit | Flat-Globose | "Sengana" |
| Plant density | Dense | |
| Plant vigor | Strong | "Grande" |
| Leaf: | | |
| a) Length | 115–155 mm | |
| b) Width | 100–115 mm | |
| c) Color | | |
| 1) Upper Side: | Medium to Dark Green | |
| d) Blistering | Medium | |
| e) Cross-section | Concave | |
| f) # of leaflets | Sometimes >3 | |
| Terminal leaflet | | |
| a) Length/Width ratio | Longer thn Borad | |
| b) Shape of base | Obtuse | |
| c) Shape of teeth | Obtuse | |
| d) Length | 50–65 mm | |
| e) Width | 50–60 mm | |
| Flower | | |
| a) Size | Large | |
| b) Size of calyx to corolla | Similar to Large | |
| c) Size of inner calyx versus outer calyx | Similar | |
| d) Spacing of petals | Overlapping | |
| e) Diameter | | |
| 1) First order | 30 mm | |
| 2) Second order | 25 mm | |
| f) Petal length/width | As Long as Broad | |
| 1) length 11–14 mm | | |
| 2) width 11–15 mm | | |
| g) Time of flowering | Very early | "Karina"[c] |

TABLE 1-continued

PLANT CHARACTERISTICS OF "VIRGINIA"

| MORPHOLOGICAL TRAIT | DESCRIPTION[a] | COMPARABLE VARIETY[b] |
|---|---|---|
| Petiole | | |
| a) Pose of hairs | Outwards | |
| b) Length | 55–90 mm | |
| Fruiting truss: | | |
| Attitude | Prostate | |
| Inflorescence | | |
| a) Position relative to foliage | Above | |

[a]The description of "Virginia" is based on the test guidlines for *Fragaria* L. of the International Union for the Protection of New Plant Varieties, (UPOV).

[b]Only characteristics which are relevant for comparing varieties are listed. For example, there are no varietal differences acknowledged in the characteristic "color of lower side of leaf".

[c]"Virginia" flowers at the end of October. One of the earliest known varieties for comparison is "Karina", which flowers in January. Additionally, "Virginia" flowers within approximately the time range as strawberry varieties "Shalom" (U.S. Plant Patent 7876), "Smadar" (U.S. Plant Patent 7865), "Saaid" (U.S. Plant Patent 7870), "Dorit" (U.S. Plant Patent 7869), "Sharon" (U.S. Plant Patent 7881), as well as "Ofra" and "Nama", described in U.S. Plant Patent Application Ser. No. 07/823,638, filed Jan. 22, 1992, and U. S. Plant Patent Application Ser. No. 07/823,721, filed Jan. 22, 1992, respectively.

TABLE 2

FRUIT CHARACTERISTICS OF "VIRGINIA"

| CHARACTERISTICS | DESCRIPTION |
|---|---|
| Time of ripening | Very Early |
| Ratio of length/maximum width | Longer than broad |
| Size | Large |
| First Order | |
| a) Predominant Shape | Wedged |
| b) Length | 40–50 mm |
| c) Width | 34–42 mm |
| d) Thickness | 30–38 mm |
| e) Weight | 23 g |
| Second Order | |
| a) Predominant Shape | Wedged |
| b) Length | 34–44 mm |
| c) Width | 32–38 mm |
| d) Thickness | 25–32 mm |
| e) Weight | 19 g |
| Difference in Shape Between First Order and Second Order Fruit | None or Very Slight |
| Band without achenes | Narrow |
| Unevenness of surface | Absent or very weak |
| Color | Red |
| Evenness of color | Even |
| Glossiness | Strong |
| Insertion of achenes | Below surface |
| Insertion of calyx | At Level |
| Pose of calyx segments | Reflexed |
| Size of calyx in relation to fruit diameter | Similar |
| Adherence of calyx | Strong |
| Firmness | Medium Firm |
| Color of flesh | Red |
| Evenness of flesh color | Slightly uneven |

TABLE 3

COMPARATIVE SHELF-LIFE AND FLAVOR OF "VIRGINIA"

| Variety | Percentage Health | Percentage Pressure defects | Firmness[a] Visual | Firmness[a] Newton units | Sepal appearance[b] | Fruit color[c] | Marketable appearance[d] | Sugar content T.S.S.[e] |
|---|---|---|---|---|---|---|---|---|
| | | | First test: at harvest date | | | | | |
| Virginia | 100 | 0 | 5 | 4.2 | 5 | 3.5 | 4.0 | 8.5 |
| Ofra[f] | 100 | 0 | 5 | 6.0 | 5 | 4.0 | 4.5 | 9.6 |
| Nama[g] | 100 | 0 | 5 | 3.7 | 5 | 3.5 | 4.0 | 8.0 |

TABLE 3-continued

COMPARATIVE SHELF-LIFE AND FLAVOR OF "VIRGINIA"

| Variety | Percentage Health | Percentage Pressure defects | Firmness[a] Visual | Firmness[a] Newton units | Sepal appearance[b] | Fruit color[c] | Marketable appearance[d] | Sugar content T.S.S.[e] |
|---|---|---|---|---|---|---|---|---|
| Douglas[h] | | | | | | | | |
| | 100 | 0 | 5 | 3.7 | 5 | 4.5 | 4.0 | 6.5 |
| Second test: | | | | | | | | |
| After 3 days of storage at 2° C. | | | | | | | | |
| Virginia | 80 | 20 | 3.5 | 3.5 | 4 | 4.2 | 3.8 | |
| Ofra | 92 | 8 | 4.0 | 6.0 | 4 | 4.2 | 4.4 | |
| Nama | 78 | 22 | 3.5 | 3.0 | 4 | 4.0 | 3.7 | |
| Douglas | | | | | | | | |
| | 76 | 24 | 3.7 | 3.5 | 4 | 5.0 | 3.7 | |
| Third test: | | | | | | | | |
| after 3 days storage at 2° C. plus 2 additional days at simulated shelf temperature of 18° C. | | | | | | | | |
| Virginia | 50 | 50 | 3.0 | 2.8 | 3.0 | 4.5 | 3.2 | |
| Ofra | 55 | 45 | 3.5 | 5.5 | 3.2 | 4.5 | 3.5 | |
| Nama | 44 | 56 | 3.0 | 3.0 | 3.0 | 4.5 | 3.0 | |
| Douglas | 45 | 55 | 3.0 | 3.0 | 3.2 | 5.0 | 3.2 | |

INDEX:
[a]5-hard 1-soft
[b]5-green, fresh like, 1-dry, brown
[c]5-dark red, 1-green, pink
[d]5-prime 1-not marketable
[e]Total Soluble Solids (T.S.S.) expresses fruit sweetness and was determined with a refractometer
[f]U.S. Plant Patent Application Ser. No. 07/823,721, filed January 22, 1992.
[g]U.S. Plant Patent Application Ser. No. 07/823,721, filed January 22, 1992.
[h]U.S. Plant Patent No. 4,487

What is claimed is:

1. A new distinct variety of strawberry plant substantially as illustrated and described and distinguished as being able to grow in September and produce fruit starting in November and lasting until summer, with fruit having a good taste and shape and a long shelf life.

* * * * *